United States Patent
Hanft (10) Patent No.: US 12,213,901 B2
(45) Date of Patent: Feb. 4, 2025

(54) NON-WATER-ACTIVATED CAST

(71) Applicant: LEG DEFENDER, LLC, South Miami, FL (US)

(72) Inventor: Jason R. Hanft, South Miami, FL (US)

(73) Assignee: LEG DEFENDER, LLC, South Miami, FL (US)

(*) Notice: Subject to any disclaimer, the term of this patent is extended or adjusted under 35 U.S.C. 154(b) by 28 days.

(21) Appl. No.: 18/083,200

(22) Filed: Dec. 16, 2022

(65) Prior Publication Data
US 2023/0122424 A1    Apr. 20, 2023

Related U.S. Application Data (62) Division of application No. 16/047,733, filed on Jul. 27, 2018.

(51) Int. Cl.
*A61F 5/00* (2006.01)
*A61F 5/01* (2006.01)

(52) U.S. Cl.
CPC ........... *A61F 5/0111* (2013.01); *A61F 5/0109* (2013.01)

(58) Field of Classification Search
CPC ........ A61F 5/011; A61F 5/109; A61F 5/0113; A61F 5/0118; A61F 5/0106; A61F 5/0104; A61F 5/0102; A61F 5/0127; A61F 5/013; A61F 5/0195; A61F 5/05825; A61F 5/05841; A61F 5/0585; A61F 5/05858; A61F 5/05866; A61F 2013/00234; A61F 13/04; A61F 13/041; A61F 13/043; A61F 13/045; A61F 13/048; A61F 13/06; A61F 13/062; A61F 13/064; A61F 13/066

USPC .......................................................... 602/27
See application file for complete search history.

(56) References Cited

U.S. PATENT DOCUMENTS

| 3,176,685 | A | * | 4/1965 | Smarook | A61F 13/04 D24/190 |
| 3,232,289 | A | * | 2/1966 | Zimmerman | A61F 5/0585 D24/190 |
| 5,584,800 | A | * | 12/1996 | Scholz | A61L 15/07 602/8 |
| 6,613,006 | B1 | * | 9/2003 | Asherman | A61F 13/04 602/8 |

(Continued)

FOREIGN PATENT DOCUMENTS

| EP | 3222256 | * | 9/2017 | ............. A61F 5/058 |
| FR | 2635973 | * | 9/1988 | ............. A61F 13/00 |

OTHER PUBLICATIONS

Vogt, EP 3222256, Translation (Year: 2024).*

*Primary Examiner* — Adam Baker
(74) *Attorney, Agent, or Firm* — Richard P. Gilly; RPG Law Group (57) ABSTRACT

A non-water-activatable cast has one or more layers of sheet-like material which create a combined flexibility, stiffness, or rigidity so that the cast may be manually positioned in substantial contact with a lower extremity to be received within the cast. As such, the cast is not only readily deployable by a patient, but has predetermined flexibility located and selected to control ankle movement within a therapeutically appropriate range, whether used by itself or in association with a related orthosis, such as a CAM walker. In certain applications, the cast likewise offloads or otherwise redistributes force by virtue of the rigidity of the plantar impact surface on such cast and the rigidity of other cast portions.

26 Claims, 9 Drawing Sheets

(56) References Cited

U.S. PATENT DOCUMENTS

| | | | | |
|---|---|---|---|---|
| 2002/0123709 | A1* | 9/2002 | Goble | A61F 5/0111 |
| | | | | 602/41 |
| 2002/0177797 | A1* | 11/2002 | Henderson | A61F 13/041 |
| | | | | 602/6 |
| 2006/0155226 | A1* | 7/2006 | Grim | A61F 13/041 |
| | | | | 602/8 |
| 2009/0264551 | A1* | 10/2009 | Nakasugi | A61L 15/12 |
| | | | | 522/66 |
| 2010/0100020 | A1* | 4/2010 | Fout | A61F 5/0195 |
| | | | | 602/23 |
| 2012/0101417 | A1 | 4/2012 | Joseph | |
| 2013/0035622 | A1* | 2/2013 | Schutz | A61F 5/05866 |
| | | | | 602/6 |
| 2015/0025431 | A1* | 1/2015 | Liden | A61F 5/05 |
| | | | | 602/12 |
| 2016/0213320 | A1* | 7/2016 | Shabah | A61N 1/0484 |
| 2017/0135839 | A1 | 5/2017 | Ducharme et al. | |

* cited by examiner

NON-WATER-ACTIVATED CAST

CROSS REFERENCE TO RELATED APPLICATION

The present application is a division of pending U.S. patent application Ser. No. 16/047,733 filed on Jul. 27, 2018.

FIELD

This disclosure relates to casts for use on humans, and in particular, to casts for the lower extremities.

BACKGROUND

Although casts for treating injuries to a person's lower extremities are available in a variety of configurations, they nonetheless suffer from various drawbacks and disadvantages, and the process of forming and applying casts likewise is often inefficient, time-consuming and suboptimal for the patient's biomechanics or lifestyle. For example, fiberglass casts, plaster casts, and other water-activated casts generally require water for activation or application, as well as specific timing, procedures and protocols. Such procedures generally involve immersing rolls of fiberglass tape, or plaster-of-Paris tape or strips in water, and then wrapping the lower extremity to be treated Accordingly, casts are generally applied by a trained medical professional and are likewise time-consuming and technically challenging to apply to the patient. After water-activated casts are set or otherwise applied to a patient, adjustment of size and fit often requires inefficient or difficult procedures, such as trimming or even sawing off unwanted material.

Plaster and other prior art water-activated cast materials may also be associated with undesirable weight, resistance to molding, excess stiffness, and other biomechanical characteristics that interfere with or lessen their therapeutic benefits or healing efficiencies. Prior art casts, whether or not water-activated, may be uncomfortable to wear on lower extremities due to the aforementioned excess stiffness.

Furthermore, plaster, fiberglass and other water-activated casts may not be optimal or appropriate for treating lower extremity conditions caused by diabetes, such as foot ulcers or other wounds, for a number of reasons. For example, breathability of casting may be important for certain conditions to be treated, and prior art casts often are not sufficiently breathable for such conditions. Additionally water may carry particulates of plaster and fiberglass into open wounds creating delay in wound healing and possible injury to patients.

Attempts to improve the application time, ease, or the performance of casts have achieved mixed results at best. For example, certain casting systems make use of a circumferential mesh sleeve of fiberglass for stretching and placing over the lower extremity, rather than wrapping the extremity with tape. However, such casts still generally require water activation and its attendant disadvantages. Furthermore, the expandable mesh and other biomechanical characteristics may not be sufficiently rigid or may be otherwise suboptimal to provide the desired immobilization or limited movement of the ankle or foot, or the therapeutically desired weight bearing functions and other desired pressure reduction during treatment of diabetic or other foot conditions, or during treatment of lower extremity injuries. Flexible mesh cast systems may not be rigid enough to protect the lower extremity during use, or may not be sufficiently rigid to transfer or otherwise off-load weight, pressure, or other forces during the person's gait cycle, such as during the heel-strike phase. Such fiberglass sleeve cast systems thus may not be efficient or optimal for particular treatments of lower extremity conditions of diabetics or for non-diabetic conditions such as ankle sprains, wounds, neuropathic issues, broken bones, and the like.

To address functional limitations of certain cast systems, the casts may need to be used with overlying boots or braces, thus complicating the treatment plan, increasing the risk that the patient incorrectly secures the boot or brace to the cast, and thus making treatment less therapeutically effective, less cost-effective, extending treatment time periods, and increasing the risk of complications.

SUMMARY

In one potential implementation of this disclosure, a cast for treating a lower extremity includes at least two layers of sheet-like material. The dimensions are such as to circumferentially enclose the lower extremity to be treated, and the two layers extend from an upper end of the cast which is located on the patient's leg between the knee and the ankle, and a lower end of the cast which is typically located on the patient's foot between the ankle and the toes. The layers have a combined flexibility which is selected so that the cast layers can be manually transformed from a first, pre-application configuration (that is, before being applied to the lower extremity), to a second configuration which it assumes after being applied to the lower extremity.

In one possible variation, the cast layers may consist essentially of non-water-activatable materials, and may be configured as a substantially planar or flat blank when in their pre-application configuration.

In another implementation of the current disclosure, the first, pre-application configuration comprises a hollow cylinder which defines a volume sufficiently sized so that the lower extremity can be readily received within the hollow cylinder. The second, post-application configuration is formable in response to manual force applied to reduce the volume of the hollow cylinder after the lower extremity has been received therein and so that an inner surface is in contact with the lower extremity. The pre-determined, combined flexibility of the layers of the cast is selected to permit the inner surface of the cast to maintain its substantial contact with the extremity during walking and is likewise selected to control ankle movement within a therapeutically selected range during walking on the lower extremity.

In the illustrated implementation of this disclosure, one of the layers of the cast is located to be an inner layer when received on the lower extremity. The material of such inner layer consists essentially of cushion material which is both water-resistant and yet breathable. A second layer is applied outside of the inner layer and consists essentially of semi-rigid, non-water activated fiberglass, polymeric material. In one possible implementation, the semi-rigid polymeric material comprises bands of the material previously arranged in adjacent and overlapping positions, such as those of a weave pattern to form a spica. The spica pattern comprises a series of overlaps or intersections and an opening which is positioned to be at the heel of the extremity when the cast is worn thereon. Similarly, one of the intersections of the spica is an "X" like pattern, and is located at the ankle joint of the lower extremity when the cast has been suitably positioned thereon.

The inner surface of inner layer may be in direct contact with the lower extremity or there may be a third, intervening layer of knitted fabric, such that the inner layer and outer polymeric layer contact the lower extremity indirectly, with the third layer providing the direct contact. Rather than such third layer being a stockingette as seen in prior art fiberglass casts, such third layer may possess additional physical or therapeutic properties, as discussed subsequently.

In still further implementations of the cast of this disclosure, the semi-rigid polymeric material may have further characteristics so that the resultant material of the cast is able to be weight bearing. Such weight bearing characteristics may be selected so as to be comparable to fiberglass casts and otherwise sufficient in terms of therapeutic uses to classify the cast in a suitable weight bearing category and associated medical applications. Similarly, the material of the may likewise have rigidity predetermined to offload a therapeutically significant percentage of force forward of the heel during heel strike. The flexibility of the cast may be selected to control ankle movement and off-load forces away from injured areas of the foot at therapeutic levels comparable to the biomechanical characteristics of a CAM walker, boot, brace, or other lower-extremity orthosis appropriate to treat the injured lower extremity.

In still another implementation of this disclosure, an orthosis, such as a CAM walker, may include a rigid frame having portions engaging one of the above-described implementations of the cast of semi-rigid material.

When combined with such an orthosis, in one possible variation, the sheet-like material of the cast may serve to immobilize the ankle by at least 50 percent as compared to the ankle's non-casted state.

BRIEF DESCRIPTION OF THE DRAWINGS

This disclosure will be detailed and explained with reference to the attached drawing, in which.

DETAILED DESCRIPTION

Figure 1:
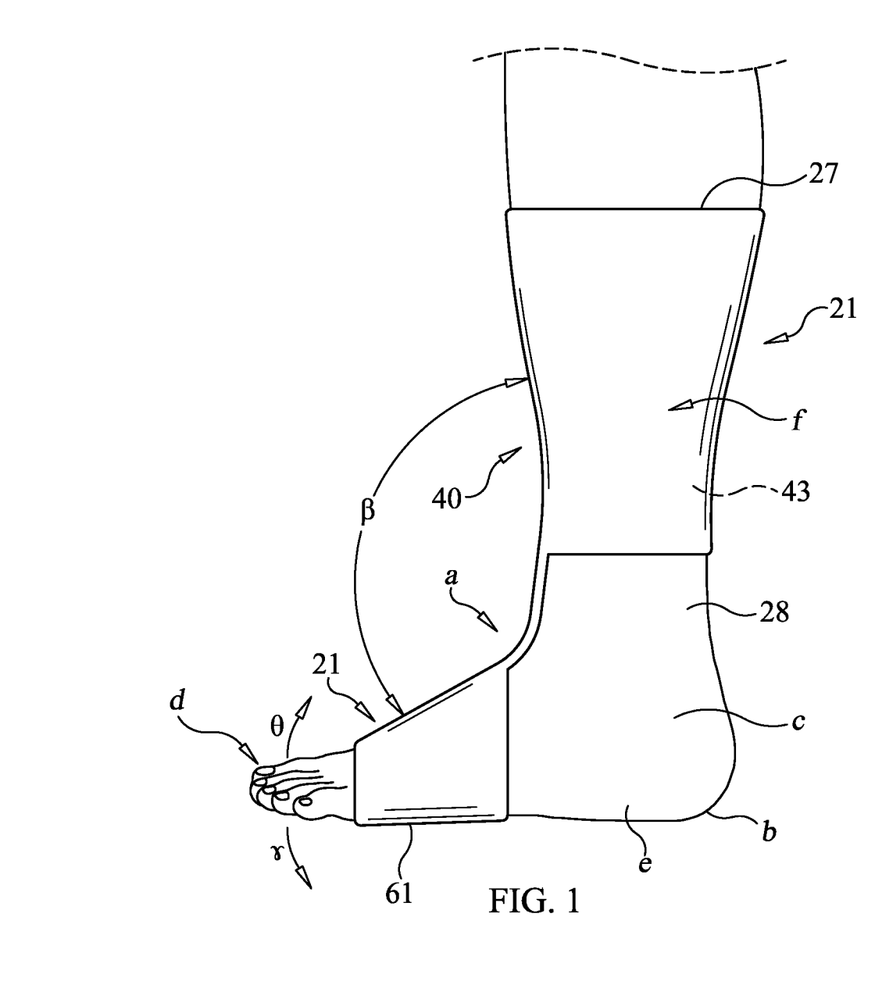
FIG. 1 is a side-elevational view of a cast according to one implementation of this disclosure being worn on a lower extremity.
Figure 2:
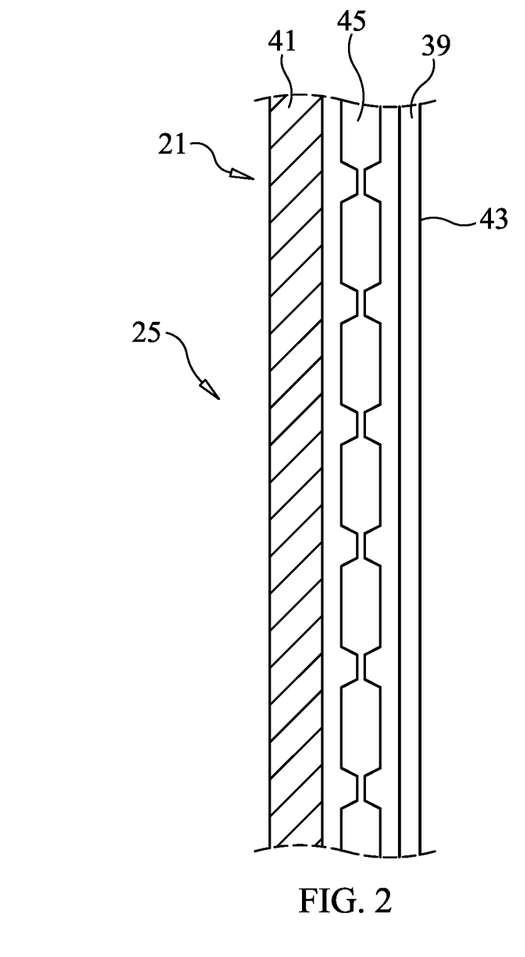
FIG. 2 is an enlarged, cross-sectional view of the layers of a cast according to one possible implementation of the present disclosure.
Figure 3:
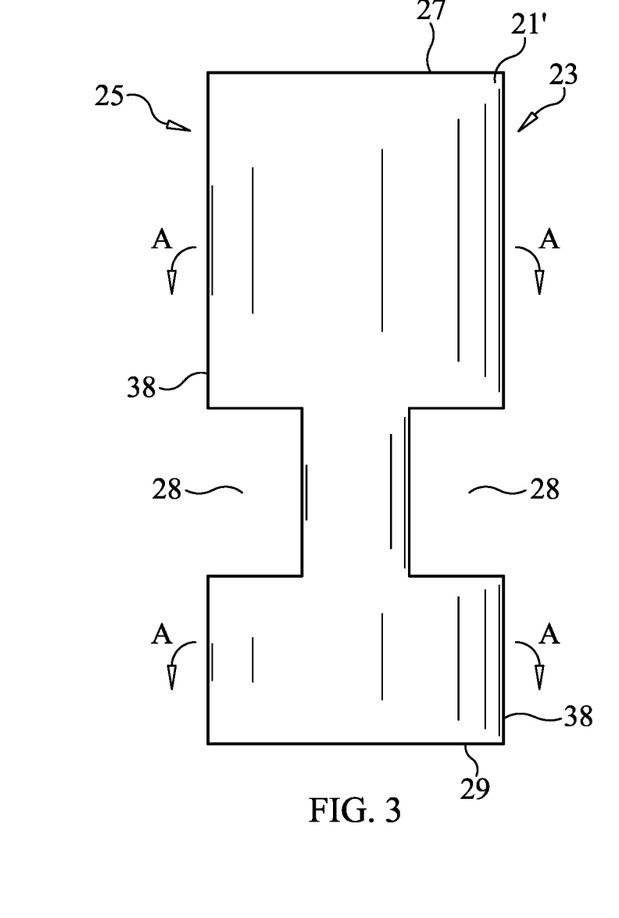
FIG. 3 is top-plan view of another possible implementation of the present disclosure.

Referring now to FIGS. 1 through 7 generally, and to the implementation shown in FIGS. 1-3 in particular, a cast 21 of the present disclosure is adapted for use on a lower extremity to be treated. The use of cast 21 and other cast implementations and variations encompassed by this disclosure may be used As explained herein, cast 21 may be applied as shown to lower extremity a without requiring water activation. One set of applications for cast 21 involves treatment of lower extremities of diabetics suffering from wounds, amputations, ulcers, and other surgeries or treatments related to the foot. Such conditions may require not only isolation and healing of wounds and injuries facilitated by casts, but potentially immobilization or limited ankle movement, off-loading of forces from heel or injured areas, such as during the gait cycle, and distribution of weight ("weight bearing") during standing and other activities. Treatment of still other lower extremity conditions benefitting from stabilization of the foot or ankle joint relative to the leg are likewise contemplated. For the sake of clarity, the use of casts disclosed herein, and their association with "treatment" or a lower extremity "to be treated," encompasses the full range of medical conditions, whether the person is wounded, injured, or at-risk of developing a wound, injury or other medical condition, and whether such condition is dermatologic, orthopedic, neurological, biomechanical, or surgical, whether for diabetics or other persons.

In the illustrated implementation, as seen in FIG. 3, cast 21 may assume a first, pre-application configuration 23, shown as a cast blank 21', in which sheet-like material 25 has dimensions to circumferentially enclose the lower extremity to be treated.

In order for material 25 to enclose a variety of sizes of lower extremities, it will be appreciated that the surface area of sheet-like material 25 may be chosen to give some slack or extra room in terms of applicable dimensions. Lower extremities may also be carrying bandaging or other surface treatments which thus may increase the circumferential size of lower extremities to be received within cast 21 and the volume defined by sheet-like material 25.

In this implementation, sheet-like material 25 terminates in an upper end 27 to be located on a patient's leg in a manner consistent with a lower-extremity cast of any suitable length that is distal to the knee and proximal to the ankle, and a lower end 29 to be located on the patient's foot. More particularly, cast 21 includes a pair of cut-outs 28 located relative to ends 27, 29 so as to expose heel b and optionally ankle c when lower extremity a is enclosed therein. The distance between upper end 27 and lower end 29 is also selected so that, when cut-outs 28 are suitably positioned about heel b/ankle c, lower end 29 terminates anterior to the ankle b and posterior to toes d. Cast 21, as illustrated in FIGS. 1-4, is an open-toe, open-heel cast.

Figure 4:
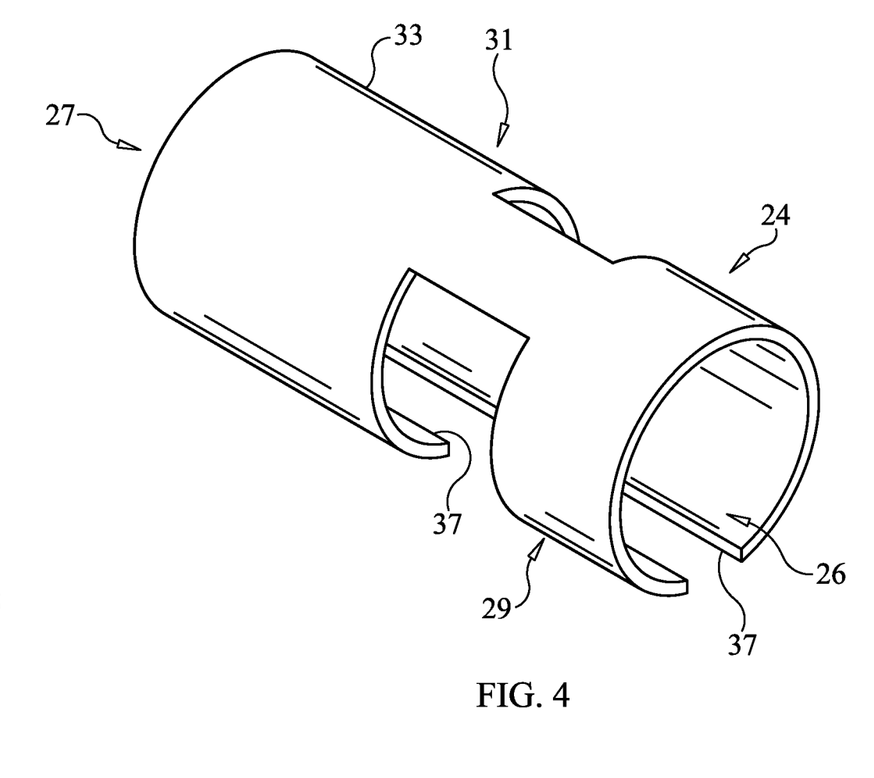
FIG. 4 is an isometric view of another possible implementation of the present disclosure.

In another implementation, seen in FIG. 4, sheet-like material 25 is of sufficient stiffness to be formed into another pre-application configuration 24 in the form of a hollow cylinder 31 which defines a volume 26 into which the lower extremity is receivable. Hollow cylinder 31 includes a cylindrical wall 33 and a longitudinally extending slit 35 formed in cylindrical wall 33 and extending between upper and lower ends 27, 29 of cast 21. As such, slit 35 defines opposing edges 37.

In the illustrated implementation, sheet-like material 25 comprises at least a first layer 39 and a second layer 41 (FIG. 2) of the sheet-like material 25, the layers 39, 41 having a pre-determined combined flexibility selected so that the layers are manually transformable from a, pre-application configuration, such as shown at 23 (FIG. 3), 24 (FIG. 4) to a second, post-application configuration 40 (FIG. 1) in contact with the lower extremity when received therein.

Sheet-like material 25 and its at least two layers 39, 41 have a predetermined combined flexibility, in particular, so that side edges 38 of cast blank 21' may be manually displaced in the directions indicted by arrows A, generally orthogonally to the plane of blank 21'. By such displacement, opposite side edges 38 are brought adjacent to or overlapping each other as they are applied around the circumference of the lower calf and foot to form post-configuration 40 shown in FIG. 1. Furthermore, the pre-determined flexibility of sheet-like material 25 and its two layers 39, 41 is selected so that, when in pre-application configuration 24, opposing edges 37 of cylindrical wall 33 may be manually parted or separated from each other at slit 35 by a sufficient amount so that cylinder 31 may be positioned around the lower extremity by receiving the lower extremity into the expanded slit 35. Thereafter, by manually urging opposing edges 37 toward each other, volume 26 enclosed by cylindrical wall 33 is lessened and inner surfaces 43 of the cylindrical wall 33 are brought into substantial contact with the lower extremity received therein.

In one possible implementation, cast 21 and all of its layers consist essentially of material that is non-water-activatable. More generally, cast 21 is formed to consist essentially of material which enables the end-user or medical professional to apply cast 21 to a lower extremity by manipulation of material 25 itself, without need for water or other curative agents, and without the need to add additional time for setting of the casting material, as in the case of plaster and other comparable materials.

As such, the first layer 39 may comprise an inner layer comprising a water-resistant or waterproof flexible material, optionally including some cushioning material and some breathability characteristics, such inner layer in substantial contact with the lower extremity and having inner surface 43 in contact (direct or indirect) with such lower extremity. Second layer 41 is disposed to the outside of first layer 39, directly or indirectly overlying first layer 39. In certain implementations, outer, second layer 41 may consist essentially of bands of semi-rigid, non-water-activated polymeric material, such as vinyl, arranged in a suitable weave pattern, such as a pattern to form a spica. The spica would comprise a series of intersections and at least one opening, such opening being locatable at the heel of the extremity when received therein and at least one of the intersections of the spica being advantageously positioned at one or more points on the ankle joint of the lower extremity. Second layer 41 may comprise one or more materials selected from the group consisting of vinyl, elastic, PVC, paper, rubber, plastic, polyethylene, and other polymeric materials, flexible metal, wood fibers and pulp-based derivatives, flexible ceramic components, nylon, knitted or technical fabrics, tapes, including bands of any of the foregoing, elasticized plaster, pre-formed fiberglass, and alginate.

Layers 39, 41 may be suitably adhered to each other, fused, sputtered, flocked, or otherwise processed to form a two-layer composite and thus substantially resemble a single layer. Such fusion and integration of the characteristics identified above for layers 39, 41 is within the scope and definition of the two layers when referred to herein and within the scope of this disclosure. Suitable adhesive may likewise be used between opposing surfaces of adjacent layers, or as a separate adhesive layer. In addition, layer 39 may have its inner surface equipped with fugitive or other adhesive having a tack appropriate for contact with the skin and removal therefrom without inappropriate discomfort, such tack likewise being sufficient to assist in maintaining inner surface 43 in substantial contact with underlying portions of the lower extremity received in cast 21.

Similarly, a third, intermediate layer 45 may be interposed between inner layer 39 and outer layer 41, such intermediate layer 45 providing any number of desirable properties, whether adding to the composite flexibility or stiffness of overall cast 21, providing padding, or providing wicking, water-resistant or waterproof characteristics. In one variation, cast 21 comprises three layers 39, 45, 41 wherein the inner layer 39 is a water-resistant, breathable material, such as GORTEX, intermediate layer 45 is of material serving primarily a padding function, and outer layer 41 is vinyl or other polymeric material, with the majority of flexibility or stiffness being provided by such outer layer 41. For this three-layer implementation, the average thickness may range (in millimeters ("mm")) from 15 mm to 35 mm, generally, and from 9.5 mm to 15 mm for applications where less weight-bearing or off-loading is needed. Outer layer 41 may comprise two layers of vinyl bands, each layer having respective thickness of 0.4 to 0.5 mm, so that layer 41 has a thickness of 0.8 to 1.0 mm, or one such vinyl layer may be used in other applications. An outer layer 41 of semi-rigid polymeric material ranging from 0.4 to 4.0 mm has been found suitable for many treatment protocols, including those associated with diabetic injuries, wounds, or at-risk conditions, but also encompassing non-diabetic conditions.

Further variations and dispositions of multiple layers of sheet-like material 25 are likewise within the scope of the current disclosure. Likewise, the overall or average thicknesses of cast 21 or other implementations within the scope of this disclosure may be below or above the ranges stated for the above-described implementation, so long as the semi-rigidity of the resulting sheet material 25 permits manipulation from a pre-application configuration to a post-application configuration around the extremity, in which the therapeutically desired immobilization or weight-bearing is achieved.

When a layer of cast 21 is described herein as being in "contact" with, or "overlying" the lower extremity, unless the context indicates otherwise, such description includes both direct and indirect contact, such that the layer operates as intended. Thus, for example, the foregoing three layers 39, 45, 41 are each in "contact" with opposing portions of lower extremity a, as each imparts its characteristics thereto, including one or more of water-resistance, padding/protection, and immobilization.

Similarly, it will be appreciated that other intersecting weave patterns besides a spica are suitable for either outer layer 41 or first layer 39, as are any number of overlapping configurations of tape, bands of material, and the like. Second layer 41 and its polymeric material, as well as layers 39, 45 may also be in a non-weave pattern or not formed of bands, but rather be formed of a substantially uniform, composite, woven or formed material.

Whatever the weave, pattern, uniformity, composition, layering, or other physical characteristics of sheet material 25, the resultant cast 21 is formed with a combined, pre-determined flexibility not only to remain in substantial contact with the underlying lower extremity a, but also to substantially control movement of ankle c, especially relative to leg f, within a therapeutically desired range, to off-load forces away from heel b or other pressure points, and to bear sufficient weight, based on therapeutic needs. The appropriate, therapeutically selected range will vary depending on the lower extremity condition being treated.

For certain lower extremity conditions, the foregoing therapeutic goals or a desired amount of pain relief may be accomplished by having the mechanical properties of resultant cast 21 include sufficient rigidity or stability of material 25 so that cast 21 substantially remains in its post-application configuration 40 except for a therapeutically acceptable range of movement of ankle c (or other lower extremity anatomy) during walking, standing, and other anticipated activity involving the lower extremity. In certain cases, the rigidity or stability of cast 21 achieves immobilization, pressure relief, off-loading, and the other desired therapeutic or pain-relief goals without requiring a separate splint, CAM walker, boot, brace, or other lower-extremity orthosis appropriate to treat the injured lower extremity to hold material 25 in position.

In other cases, cast 21 has a combined flexibility pre-determined to achieve a level of immobilization by resisting movement about ankle c and maintain post-application configuration 40 during most anticipated activities, while using cast 21 in combination with a splint, CAM walker, boot, brace, or other lower-extremity orthosis appropriate to treat the injured lower extremity to provide pressure relief or off-loading to the lower extremity being immobilized by the rigidity of cast 21. So if cast 21 has been fitted to lower extremity a in the neutral position shown in FIG. 1, in which foot e forms an angle $\beta$ of about 90° with leg f, the pre-determined flexibility of cast 21 restricts motion of ankle c (and related anatomy of lower extremity a) to a therapeutically acceptable range during a therapeutically determined percentage of anticipated patient activity. Among the orthopedic motions of potential therapeutic interest to limit by means of cast 21 would be the degrees of plantar flexion $\gamma$ and dorsiflexion $\theta$.

Figure 14:
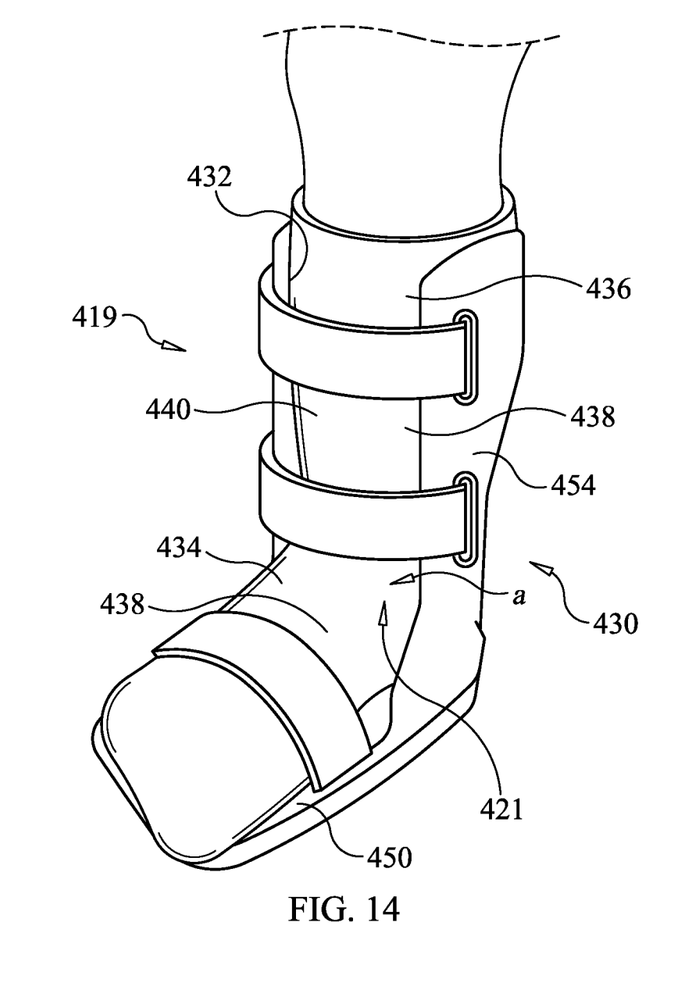
FIG. 14 is a front isometric of another possible implementation of the present disclosure.

As seen in FIG. 14, in a version of cast 21 used with a lower-extremity orthosis, such as a CAM walker 419, while a certain amount of weight-bearing and off-loading may be accomplished by cast 21, additional weight-bearing and off-loading may be accomplished by CAM walker 419.

While the mechanical properties of sheet-like material 25, cast 21 and other aspects of this disclosure are described using the term "flexibility," mechanical properties of cast 21 and its material 25 may be expressed using complementary and related mechanical properties of cast 21 and its material 25, such as the complement of flexibility, namely rigidity, stiffness or resiliency. Flexibility and stiffness may be determined and expressed as a function of one or more degrees of freedom, and in terms of moments of force. As such, flexibility and rigidity of portions of material 25 of cast 21, whether located at, or proximal, distal, lateral or medial of the ankle joint, may be characterized in terms of resistance to dorsal, plantar, lateral, or medial flexion at the ankle joint, as well as eversion or inversion of the foot.

Similarly, rigidity of the portions of cast 21 located on plantar surface 161 (Fig. of the foot may be expressed in terms not only of rigidity, but also in terms of their capacity to off-load a force at one plantar location to another, such as from the heel toward the mid-foot, or to bear or distribute weight so as to relieve pain points on the foot. Otherwise stated, flexibility and rigidity may be in relation to moments of force, compressive forces, tensile forces, shear forces, tangential, orthogonal, or other force vectors, or resistance to such forces. Flexibility and rigidity as applied to sheet material 25 and cast 21 may be designed, determined, or selected by reference to established ASTM or ISO standards associated with casts or lower-extremity orthoses. As such, the biomechanical properties of cast 21 and sheet-like material 25 are likewise quantifiable using the same metrics currently used for evaluating properties and performance of current casts, immobilizing devices, boots, or braces, such as CAM walkers, or other lower-extremity orthoses appropriate to treat the lower extremity.

In a further variation of this disclosure, there may be a plurality of casts 21, each having an associated, pre-determined flexibility associated therewith, so that a practitioner may select an appropriate one of the casts 21, and form it from its pre-application configurations 23, 24 to its second, post-application configuration 40, and thus have associated therewith the pre-determined flexibility of material 25 for the therapeutically desired range of motion for the condition being treated.

In still further implementations, it will be appreciated that the pre-determined, combined flexibility for a given portion of cast 21 may vary depending on its location on blank 21' or cylindrical wall 33 relative to ends 27, 29. Thus, for example, those portions of sheet-like material 25 likely to be subjected to increased bending moments or other forces during walking or other activity of the lower extremity, such as plantar impact surface 61 (FIG. 1) may be designed to have increased rigidity (less flexibility) at or adjacent to such regions to maintain the substantial contact, the therapeutically desired range of ankle movement, or the other desired therapeutic benefits to cast 21.

Second layer 41, or the combined flexibility of sheet material 25, may be selected so that cast 21 is suitable for bearing weight or distributing downward force of the user, such as when standing. With reference to the kinetics of the gait cycle, the flexibility (or its complementary property of rigidity) may be such as to offload a therapeutically significant percentage of force forward of the heel, or to bear weight or distribute force of the user during heel strike, toe-off, propulsive, or other phases of the gait cycle. The flexibility and rigidity of cast 21 may be selected to control ankle movement during the gait cycle at levels comparable to those of a water-activated cast or to those of a CAM walker or any number of boots, braces, or other lower-extremity orthoses appropriate to treat the lower extremity, and may likewise bear/transfer weight, thereby eliminating the need to use such braces and boots. Again, though cast 21 may permit a lower extremity received therein to become weight-bearing and otherwise not require additional bracing or support structure, this disclosure is not so limited, and the cast 21 herein may be used in conjunction with other orthoses, such as a CAM walker, boot, brace, or other lower-extremity orthosis appropriate to treat the lower extremity.

Cast 21 may be implemented to include another layer, either adhered or otherwise fused to inner surface 43 of inner layer 39 or manually separable therefrom, forming a lining or sock (not shown). In one suitable implementation, this lining or sock comprises knitted or non-woven technical fabric or fabrics, the fabric configured to have properties which benefit treatment of the lower extremity received therein. The lining or sock may be in direct contact with the lower extremity, such that overlying inner layer 39 (and outer layer 41) are in indirect contact with such lower extremity. The lining or sock may have anti-microbial properties, insulative properties, wicking properties, or anti-friction properties, or any combination of the foregoing.

As such, in one implementation, not only does cast 21 consist essentially of material that is non-water-activatable, but also such cast comprises the following layers of sheet-like material, whether separable or fused together, the four layers circumferentially enclosing and disposed relative to the lower extremity, from innermost to outermost as follows:

a lining or sock, layer 39 of water-resistant/waterproof material layer 45 of padded material, and semi-rigid layer 41.

Variations to pre-application configuration 23 are contemplated by this disclosure, such that material 25 need not be in the planar form of blank 21' or cylindrical form 31, may not require slit 35, and may not be pre-formed. For example, the cast layers 39, 41 may be tightly rolled when in their pre-application configuration. Pre-application configurations may likewise include more than one piece, such as one flat or cylindrical piece for the leg and one for the foot, such multiple pieces having portions designed for overlapping at the ankle. Still other pre-application configurations are possible.

Figure 5:
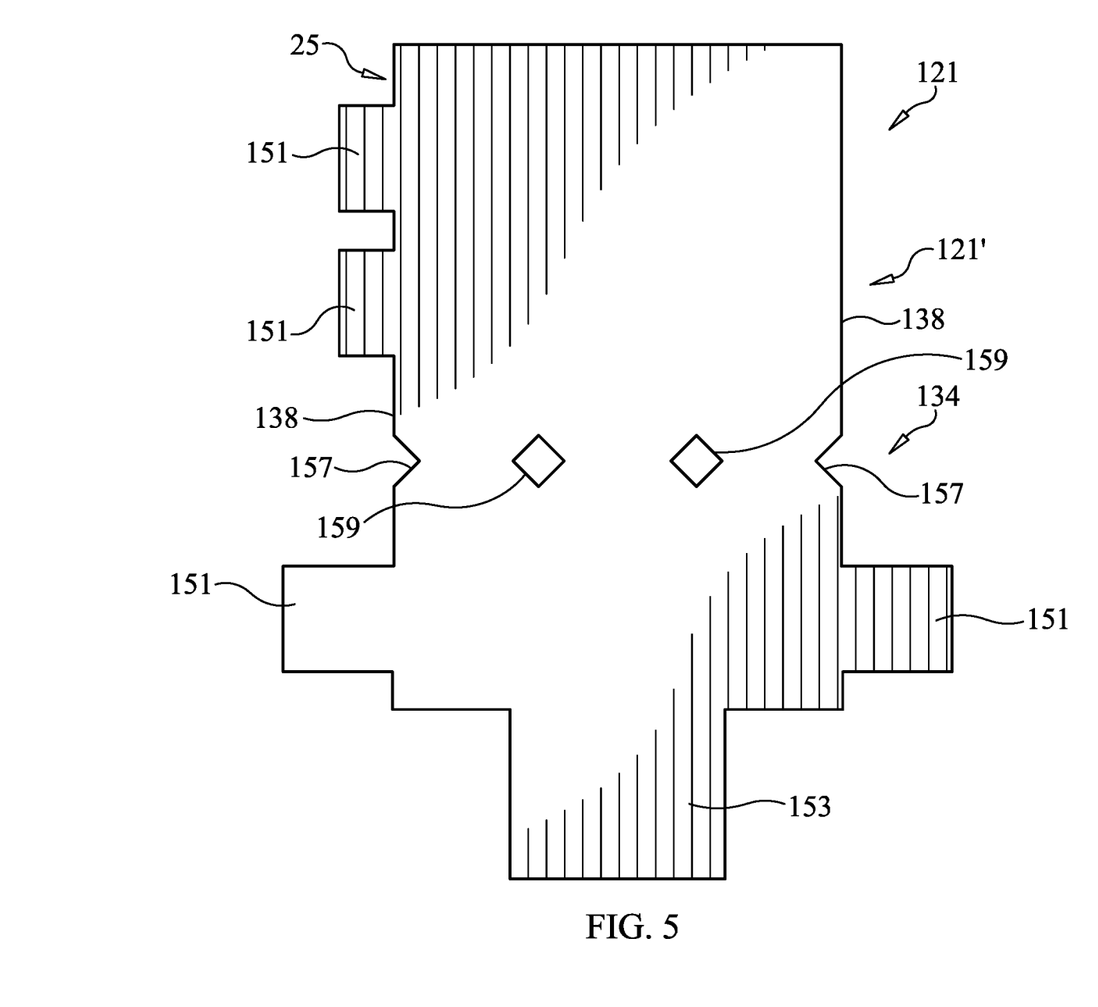
FIG. 5 is a top-plan view of still another possible implementation of the present disclosure.
Figure 6:
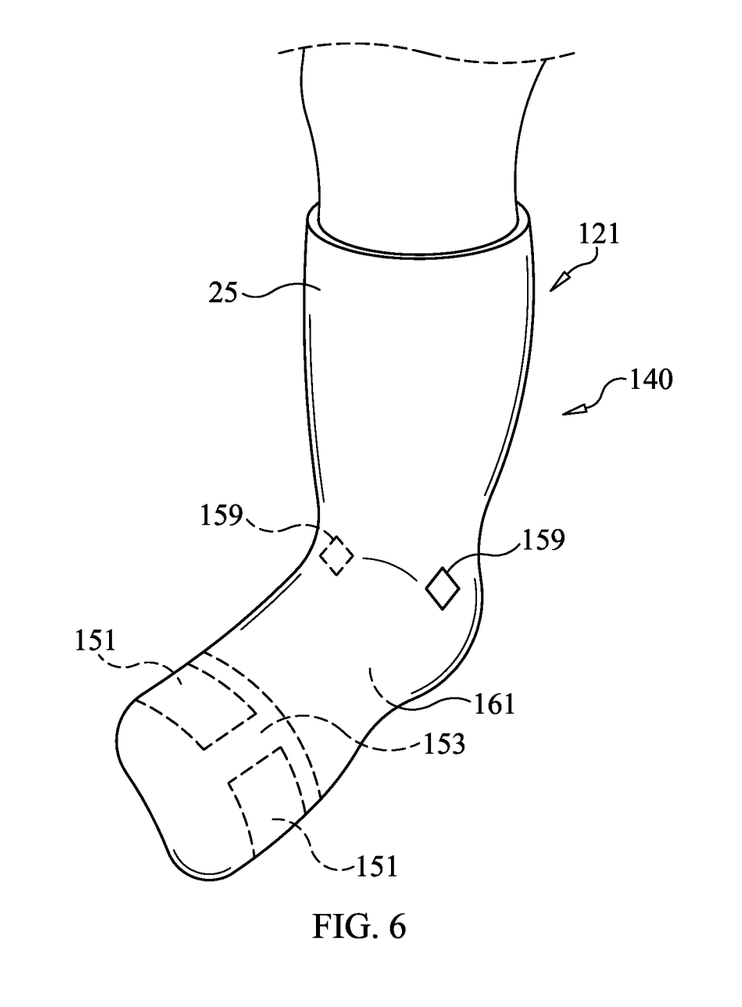
FIG. 6 is a front isometric view of the implementation of FIG. 5 worn on a lower extremity.
Figure 7:
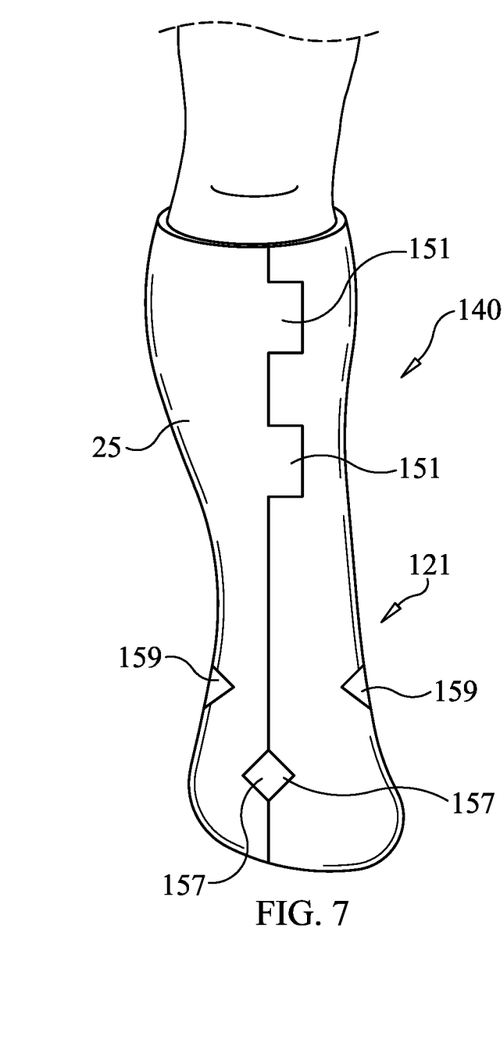
FIG. 7 is a rear elevational view of the implementation of FIGS. 5 and 6.

In still other implementations, referring more particularly to FIGS. 5-7, cast 121 and its corresponding blank 121' may have sheet material 25 (with a variety of functional layers as described with reference to FIGS. 1-4, especially FIG. 2. Sheet material 25 is arranged so as to include one or more tabs 151, may exclude the cut outs 28 shown in the embodiment of FIGS. 1-4, and may include a foldable section 153 which can be disposed anteriorly around the toes. As such, sheet material 25 may assume a pre-application configuration 134 corresponding to blank 121' and a post-application configuration 140, corresponding to the closed toe, closed heel arrangement shown. Two apertures 159 are suitably sized and located on blank 121' to potentially receive all or part of the malleoli of ankle c therein when cast 121 has been transformed into its post-application configuration 140 engaging lower extremity a, with the goal of improving fit or comfort. Similarly opposite sides 138 have been provided with detents 157 to potentially become located above the heel proximate to the Achilles tendon when in its post-application configuration 140 with the goal of improving fit or comfort. As such, cast 121 and its corresponding blank 121' form a closed heel, closed toe configuration as shown in FIGS. 6 and 7.

Figure 8:
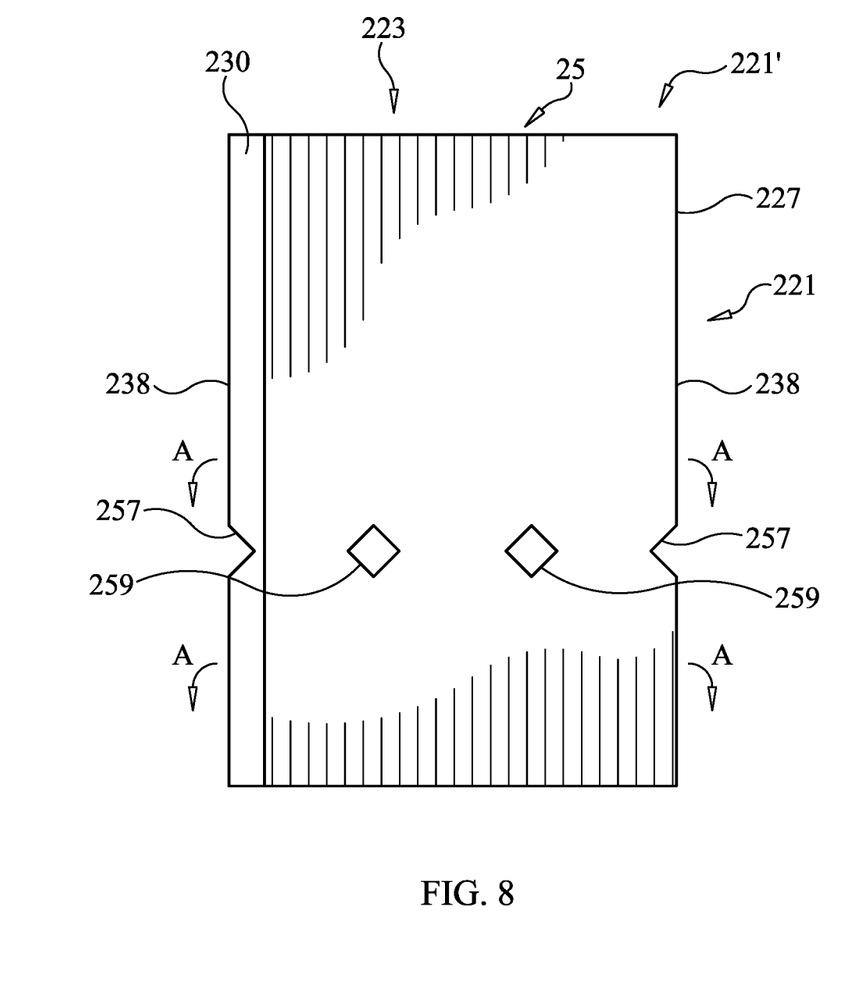
FIG. 8 is a top-plan view of a closed-heel, open-toe implementation of the present disclosure.
Figure 9:
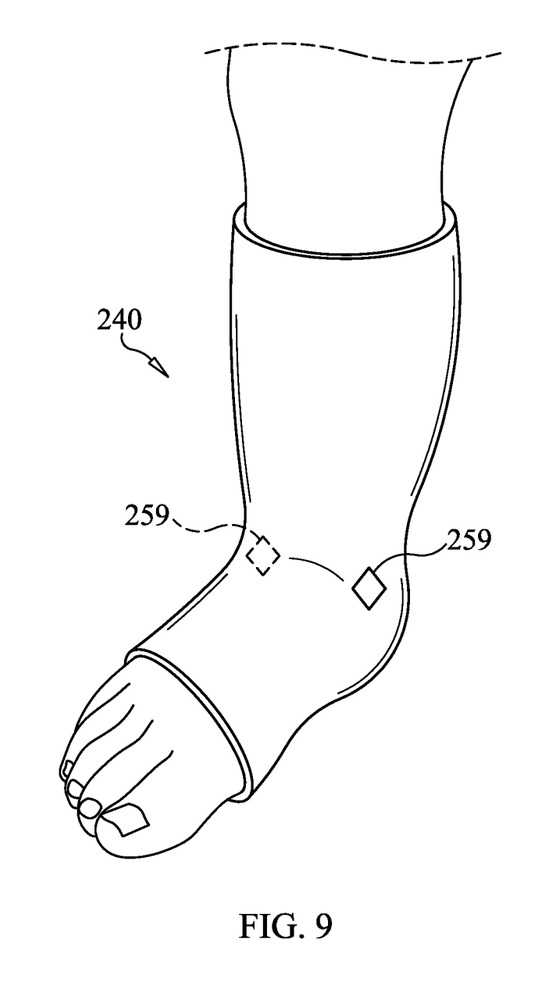
FIGS. 9-10 are front, isometric and rear elevational views, respectively, of the implementation of FIG. 8, worn on a lower extremity.
Figure 10:
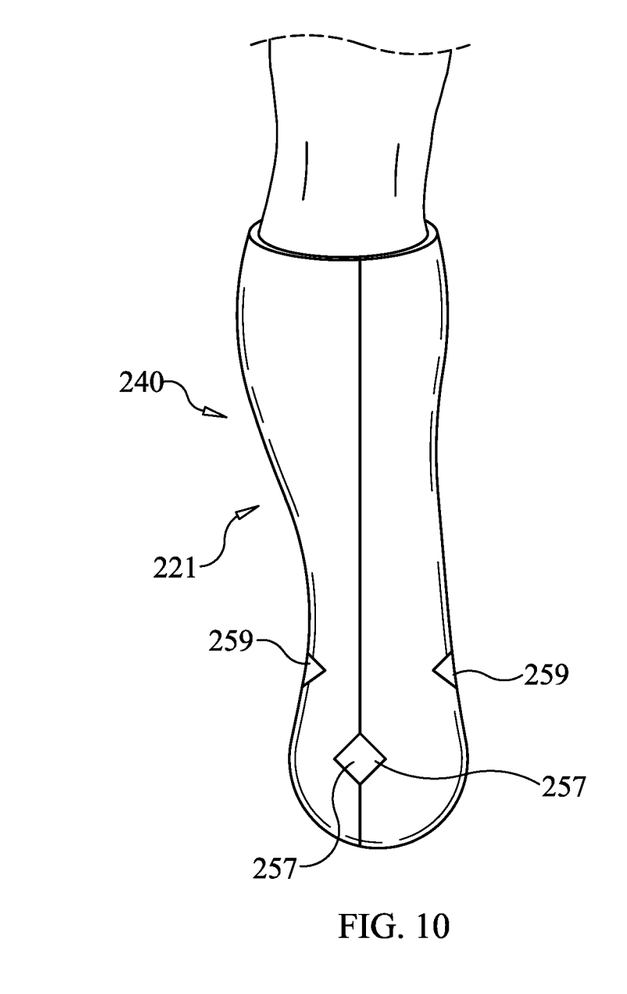

Still further implementations of this disclosure may enclose or expose heel, toe and other portions of lower extremity a to effectuate desired treatments. As such, referring to FIGS. 8-10, a closed-heel, open-toe cast 221 (and corresponding blank 221') includes sheet-like material 225 having the functional layers discussed previously, such as inner and outer layers 39, 41 (FIG. 2), and upper and lower ends 227, 229 sized and located similarly to upper and lower ends 27, 29 of FIG. 3, with opposite, longitudinal side edges 238, and apertures 259 and detents 257 similar to apertures 159 and detents 157 of FIGS. 5-7. Blank 221' may be manipulated from a substantially planar pre-application configuration 223, such as by moving opposite side edges 238 generally orthogonally to the plane of FIG. 8 as indicated by arrows A, and sheet material 225 has a preselected semi-rigidity to hold its post-application configuration 240 shown in FIGS. 9 and 10. As a result, blank 221' encloses heel b, yet leaves toes d open. A self-sticking surface treatment portion 230 may be provided, here extending longitudinally along one of the side edges 238, to assist in avoiding peel back of corresponding side edge 238 when in post-application configuration 240 (FIGS. 10, 11).

Figure 11:
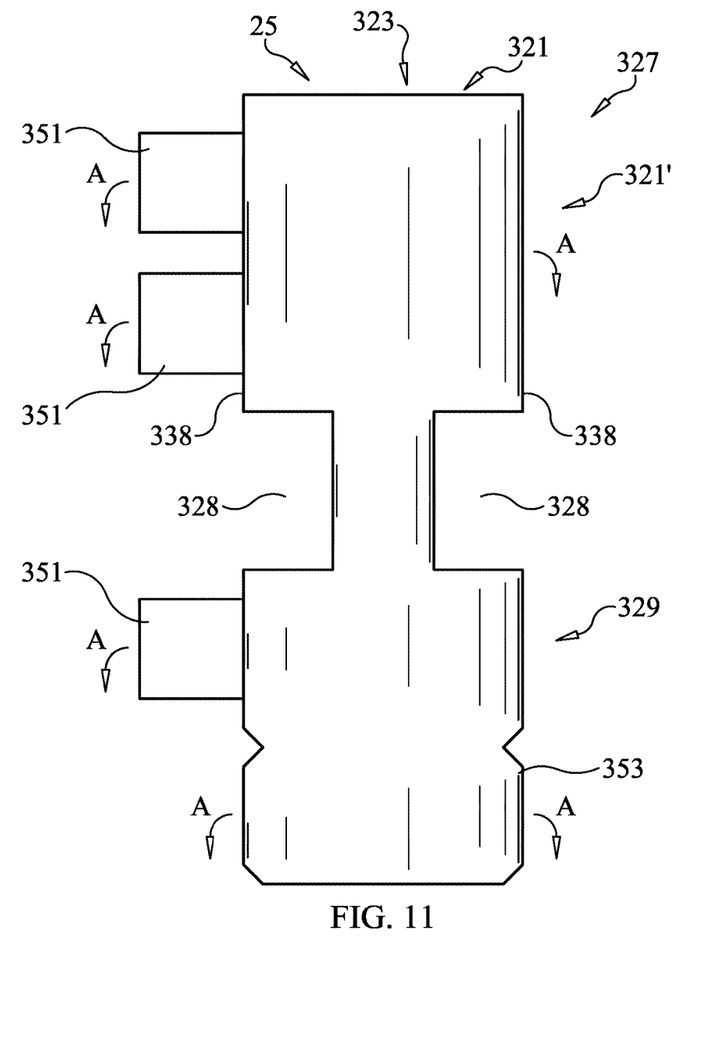
FIG. 11 is a top-plan view of a an open-heel, closed toe implementation of the present disclosure.
Figure 12:
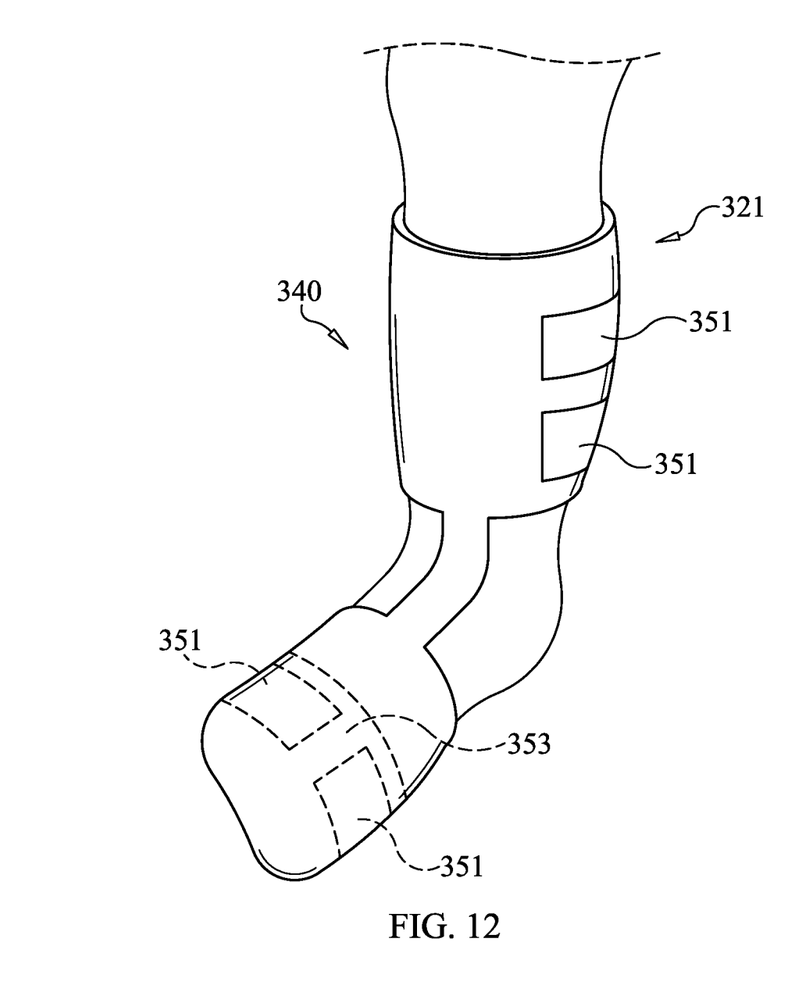
FIGS. 12-13 are front isometric and rear elevational views, respectively, of the implementation of FIG. 11.
Figure 13:
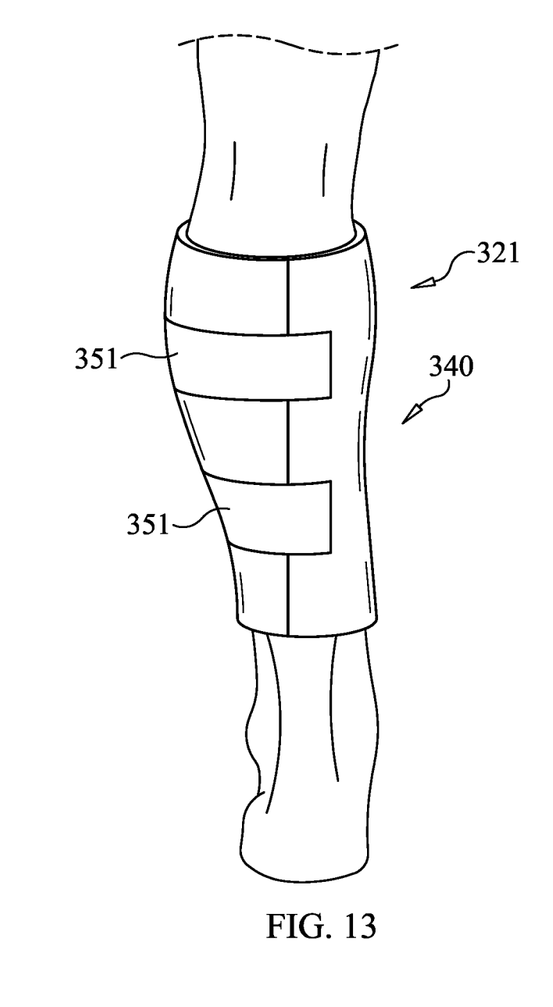

Referring to FIGS. 11-13, an open-heel, closed-toe cast 321 (and corresponding blank 321') includes upper and lower ends 327, 329 sized and located as discussed with reference to the previous implementations, including cut-outs 328 to generate an opening about heel b but toe portion 353 is manually moveable to enclose toes d, as shown. Blank 321' is composed of sheet material 25 (like reference numbers throughout this disclosure referring to like elements in previously described implementations). Similarly, variations on previously described features have been given corresponding reference numbers with respect to cast 321, including cut-out portions 328 to expose the heel when received therein, tabs 351, and side edges 338. As previously described, blank 321' may be manipulated into a post-application configuration 340 (FIGS. 12-13) from pre-application configuration 323 (FIG. 11).

An orthosis 419 incorporating features of the casts described herein is shown in FIG. 14. Orthosis 419 in this implementation comprises a CAM walker with a rigid frame 430 and cast 421. Rigid frame 430 has an inner surface 432 forming a volume suitable for receiving cast 421 therein. Cast 421 has features and structures as described with reference to the previous implementations of casts 21, 121, 221, or 321, including sheet material 25 as described herein. Cast 421 has been manipulated into its post application configuration 440 around lower extremity a. Cast 421 has a corresponding blank as described previously for the other implementations, formed of semi-rigid material with suitable flexibility/rigidity described above. Cast 421 has a plantar portion 434 and a leg portion 436, the portions having respective outer surfaces 438. Inner surface 432 of rigid frame 430 engages at least one of the outer surfaces 438 of the cast 421.

In one possible variation, cast 421 is formed of at least two layers of sheet-like material, with the layers having a predetermined, combined flexibility selected to have the layers manually transformable from a first, pre-application configuration in the form of the blank with side edges, such as blanks 21', 121', 221', and 321' previously discussed, before fitting on the lower extremity, to the second, post-application configuration 440 after the fitting on the lower extremity.

As in previous implementations, post-application configuration 440 is formed in response to manual force applied to the blank to bring side edges of the blank relatively toward each other to define a volume into which the lower extremity is received and to define an inner surface to substantially contact opposing portions of the lower extremity when received therein. The predetermined flexibility is selected so that cast 421, separate and apart from frame 430, limits at least one of plantar flexion, dorsiflexion, eversion, and inversion of the ankle of the lower extremity by at least 50% compared to a corresponding, non-casted movement of said ankle.

Rigid frame 430 may include a plantar support member 450 and a leg bracing member 545. Plantar support member 450 is sized so that it may receive thereon the plantar portion 434 of the cast, and the leg bracing member 545 is configured to engage the leg portion 436 of cast 421.

Testing was performed for one of cast implementations set out herein (without the related rigid orthosis), in which inner layer 39 comprises water-resistant material, layer 45 comprises padding, and outer layer 41 comprises two, 0.43 mm-thick layers of vinyl bands in a woven pattern forming a spica. It was found that the foregoing combination of non-water activated materials formed a combined flexibility to achieve desired therapeutic goals after application to a lower extremity. For example, measurements were taken of the range of motion of the ankle joint, subtalar joint, metatarsophalangeal joints, and gait analysis—all in relation to the motions of dorsiflexion, flexion, plantar flexion and inversion/eversion. The above-described testing was performed on a lower extremity having a base-line, non-casted range of motion. For the ankle joint, results/testing showed dorsiflexion limited to 90% compared to the non-casted range of motion, plantar flexion limited to 95% of the otherwise non-casted range of motion and ankle joint inversion/eversion limited to 95% compared to a non-casted range of motion. For the subtalar joint, motions were limited by more than 90% compared to non-casted. With regard to the metatarsophalangeal joints, plantar flexion was limited to 90%, while dorsiflexion was limited to 80%, the foregoing again compared to the base-line non-cast-range of motion.

With regard to the gait analysis, stride length was shortened by application of cast 21, speed of floor propulsion decreased. No true heel strike was witnessed, thereby achieving off-loading. Steppage gait occurred with contact made with substantially all of the plantar surface of the foot from the metatarsophalangeal joints proximal to the heel. Rigidity and/or flexibility of cast 21 was such as to substantially limit the range of motion at the ankle and achieve slight, circumductive gait, with subjects reporting transmission of pressure/force otherwise felt at the foot up the leg to the tibia and calf area.

Operation and use of the cast 21 is apparent from the foregoing description. A patient, medical practitioner or other third party, by manual force, is able to transform the pre-application configuration of sheet-like material 25, 134 and its multiple layers 39, 41, to a post-application configuration 40, 140 around the lower extremity to be treated as shown in FIGS. 1, and 6-7, respectively. The resultant cast 21 exhibits mechanical properties of flexibility/rigidity selected to provide control of ankle movement or substantial immobilization, weight-bearing, offloading of pressure, a therapeutic environment, and other therapeutic benefits during the biomechanics of walking or other activity.

Cast 21 may be used as part of a computer-implemented system to diagnose, analyze, or otherwise evaluate performance of cast 21 itself, as well as any associated CAM walker, boot, brace, or other lower-extremity orthosis associated with the lower extremity under treatment. Data may be gathered by associating cast 21 with sensors capable of obtaining inputs on force, pressure, temperature, acceleration and the like, when cast 21 is being worn on the lower extremity a. In one possible implementation, such sensors are deployed at suitable, corresponding locations on inner surface 43 of cast 21, such as on the portion of the inner surface opposing the plantar surface of the lower extremity received therein. Data thus gathered may be used as inputs to modify the rigidity or other parameters of cast 21, or to design or modify the design of cast 21 or of orthoses associated with the lower extremity treatment, as set out in U.S. Pat. No. 9,201,413, the contents of which are incorporated herein by reference.

The foregoing is provided for purposes of illustrating, explaining, and describing implementations of this disclosure. Thus, although specific arrangements have been illustrated and described herein, other arrangements may achieve the same or similar purposed and may be substituted for the specific arrangement shown. Combinations of the above arrangements, and other arrangements not specifically described herein, will be apparent to those of skill in the art upon reviewing the above description. Therefore, it is intended that the disclosure not be limited to the particular arrangement(s) disclosed herein, and that such alternatives and equivalents are within the spirit and scope of this disclosure, as defined in the following claims.

What is claimed is:

1. A cast for a lower extremity to be treated, the cast comprising:

at least two layers of sheet-like material, wherein the layers have a predetermined, combined flexibility selected to have the layers manually transformable from a first, pre-application configuration before fitting on the lower extremity, to a second, post-application configuration after the fitting on the lower extremity;

wherein the first, pre-application configuration comprises a blank of the sheet-like material in a semi-rigid state extending transversely between opposite side edges by a first amount sufficient to substantially, circumferentially enclose the lower extremity by manually urging said edges toward each other, the sheet-like material extending longitudinally between upper and lower ends by a second amount sufficient to locate the leg and the foot of the lower extremity at the upper and lower ends, respectively, after fitting on the lower extremity wherein the second, post-application configuration is formed in response to manual force applied to the blank to bring the side edges relatively toward each other to define a volume into which the lower extremity is received and to define an inner surface to substantially contact opposing portions of the lower extremity when received therein;

wherein the predetermined flexibility is selected to permit the inner surface of the cast to maintain the substantial contact with the lower extremity during walking on the lower extremity; and wherein the predetermined flexibility is selected to limit at least one of plantar flexion, dorsiflexion, eversion, and inversion of the ankle of the lower extremity by at least 50% compared to a corresponding, non-casted movement of said ankle.

2. The cast of claim 1, wherein each of said layers consists essentially of material that is non-water-activatable and at least one of said layers is water resistant.

3. The cast of claim 1, wherein the cast consists essentially of material that is non-heat-activatable.

4. The cast of claim 1, wherein one of the layers comprises an outer layer of semi-rigid polymeric material having a thickness ranging between 0.4 mm and 0.9 mm.

5. The cast of claim 4, wherein one of the layers comprises cushioning material.

6. The cast of claim 4, wherein the sheet-like material is characterized by a semi-rigidity selected to place the cast in a weight-bearing category in terms of therapeutic uses to offload a therapeutically significant percentage of force forward of the heel during heel strike, and to control ankle movement at therapeutic levels comparable to a CAM walker.

7. The cast of claim 4, wherein the sheet-like material is characterized by a semi-rigidity selected to place the cast in a weight-bearing category in terms of therapeutic uses to offload a therapeutically significant percentage of force of the forefoot, and to control foot movement at therapeutic levels comparable to a CAM walker.

8. The cast of claim 4, wherein one of the layers is located radially inwardly from the outer layer, and comprises knitted fabric configured to have at least one of the properties selected from the group consisting of anti-microbial properties, insulative properties, wicking properties, and anti-friction properties.

9. The cast of claim 4, further comprising at least one sensor deployed at a sensor location on the inner surface of the cast, the sensor configured to receive at least one input corresponding to at least one of force, pressure, temperature, and acceleration, the input further corresponding to a portion of the lower extremity positioned at the sensor location when the lower extremity is received in the cast.

10. A cast for a lower extremity of a patient to be treated, the cast comprising: at least two layers of sheet-like material, wherein the layers have a
predetermined, combined flexibility selected to have the layers manually transformable from a first, pre-application configuration before fitting on the lower extremity, to a second, post-application configuration after the fitting on the lower extremity;
wherein the first, pre-application configuration comprises a blank of the sheet-like material in a semi-rigid state extending transversely between opposite side edges by a first amount sufficient to substantially, circumferentially enclose the lower extremity of said patient by said patient manually urging said edges toward each other, the sheet-like material extending longitudinally between upper and lower ends by a second amount sufficient to locate the leg and the foot of the lower extremity at the upper and lower ends, respectively, after fitting on the lower extremity;
wherein the second, post-application configuration is formed in response to manual force applied to the blank to bring the side edges relatively toward each other to define a volume into which the lower extremity is received and to define an inner surface to substantially contact opposing portions of the lower extremity when received therein;
wherein the predetermined flexibility is selected to permit the inner surface of the cast to maintain the substantial contact with the lower extremity during walking on the lower extremity; and
wherein the predetermined flexibility is selected to limit at least one of plantar flexion, dorsiflexion, eversion, and inversion of the ankle of the lower extremity by at least 50% compared to a corresponding, non-casted movement of said ankle.

11. The cast of claim 10, wherein each of said layers consists essentially of material that is non-water-activatable and at least one of said layers is water resistant.

12. The cast of claim 10, wherein the cast consists essentially of material that is non-heat-activatable.

13. The cast of claim 10, wherein one of the layers comprises an outer layer of semi-rigid polymeric material having a thickness ranging between 0.4 mm and 0.9 mm.

14. The cast of claim 13, wherein one of the layers comprises cushioning material.

15. The cast of claim 13, wherein the sheet-like material is characterized by a semi-rigidity selected to place the cast in a weight-bearing category in terms of therapeutic uses to offload a therapeutically significant percentage of force forward of the heel during heel strike, and to control ankle movement at therapeutic levels comparable to a CAM walker.

16. The cast of claim 13, wherein the sheet-like material is characterized by a semi-rigidity selected to place the cast in a weight-bearing category in terms of therapeutic uses to offload a therapeutically significant percentage of force of the forefoot, and to control foot movement at therapeutic levels comparable to a CAM walker.

17. The cast of claim 13, wherein one of the layers is located radially inwardly from the outer layer, and comprises knitted fabric configured to have at least one of the properties selected from the group consisting of anti-microbial properties, insulative properties, wicking properties, and anti-friction properties.

18. The cast of claim 13, further comprising at least one sensor deployed at a sensor location on the inner surface of the cast, the sensor configured to receive at least one input corresponding to at least one of force, pressure, temperature, and acceleration, the input further corresponding to a portion of the lower extremity positioned at the sensor location when the lower extremity is received in the cast.

19. An orthosis for a lower extremity to be treated, the orthosis comprising:
a rigid frame having an inner surface;
a cast comprising a plantar portion and a leg portion, the portions having respective outer surfaces;
wherein the inner surface of the rigid frame engages at least one of the outer surfaces of the cast;
wherein the cast is formed of at least two layers of sheet-like material, wherein the layers have a predetermined, combined flexibility selected to have the layers manually transformable from a first, pre-application configuration before fitting on the lower extremity, to a second, post-application configuration after the fitting on the lower extremity;
wherein the first, pre-application configuration comprises a blank of the sheet-like material in a semi-rigid state extending transversely between opposite side edges by a first amount
sufficient to substantially, circumferentially enclose the lower extremity after manipulation of the blank, the sheet-like material extending longitudinally between upper and lower ends by a second amount sufficient to locate the leg and the foot of the lower extremity at the upper and lower ends, respectively, after fitting on the lower extremity
wherein the second, post-application configuration is formed in response to manual force applied to the blank to bring the side edges relatively toward each other to define a volume into which the lower extremity is received and to define an inner surface to substantially contact opposing portions of the lower extremity when received therein;
wherein the predetermined flexibility is selected to permit the inner surface of the cast to maintain the substantial contact with the lower extremity during walking on the lower extremity; and
wherein the predetermined flexibility is selected to limit at least one of plantar flexion, dorsiflexion, eversion, and inversion of the ankle of the lower extremity by at least 50% compared to a corresponding, non-casted movement of said ankle.

20. The orthosis of claim 19, wherein the orthosis comprises a CAM walker, and
wherein the rigid frame comprises a plantar support member and a leg bracing member, the plantar support member adapted to receive thereon the plantar portion of the cast, and the leg bracing member is configured to engage the leg portion of the cast.

21. The orthosis of claim 20, wherein the cast consists essentially of material that is non-water-activatable.

22. The orthosis of claim 20, wherein the cast consists essentially of material that is non-heat-activatable.

23. An orthosis for a lower extremity of a patient to be treated, the orthosis comprising:
a rigid frame having an inner surface;
a cast comprising a plantar portion and a leg portion, the portions having respective outer surfaces;
wherein the inner surface of the rigid frame engages at least one of the outer surfaces of the cast;

wherein the cast is formed of at least two layers of sheet-like material, wherein the layers have a predetermined, combined flexibility selected to have the layers manually transformable from a first, pre-application configuration before fitting on the lower extremity, to a second, post-application configuration after the fitting on the lower extremity;

wherein the first, pre-application configuration comprises a blank of the sheet-like material in a semi-rigid state extending transversely between opposite side edges by a first amount sufficient to substantially, circumferentially enclose the lower extremity after manipulation of the blank, the sheet-like material extending longitudinally between upper and lower ends by a second amount sufficient to locate the leg and the foot of the lower extremity at the upper and lower ends, respectively, after fitting on the lower extremity wherein the second, post-application configuration is formed in response to manual force applied by said patient to the blank to bring the side edges relatively toward each other to define a volume into which the lower extremity is received and to define an inner surface to substantially contact opposing portions of the lower extremity when received therein;

wherein the predetermined flexibility is selected to permit the inner surface of the cast to maintain the substantial contact with the lower extremity during walking on the lower extremity; and wherein the predetermined flexibility is selected to limit at least one of plantar flexion, dorsiflexion, eversion, and inversion of the ankle of the lower extremity by at least 50% compared to a corresponding, non-casted movement of said ankle.

24. The orthosis of claim 23, wherein the orthosis comprises a CAM walker, and wherein the rigid frame comprises a plantar support member and a leg bracing member, the plantar support member adapted to receive thereon the plantar portion of the cast, and the leg bracing member is configured to engage the leg portion of the cast.

25. The orthosis of claim 24, wherein the cast consists essentially of material that is non-water-activatable.

26. The orthosis of claim 24, wherein the cast consists essentially of material that is non-heat-activatable.

* * * * *